United States Patent [19]

Morgan et al.

[11] Patent Number: 4,585,755

[45] Date of Patent: Apr. 29, 1986

[54] CYCLIC AND BRIDGED CYCLIC SOMATOSTATIN ANALOGS USEFUL AS LOCAL ANTI-INFLAMMATORY AGENTS

[75] Inventors: Evan R. Morgan, Bridgewater; Sanford L. Steelman, Watchung, both of N.J.

[73] Assignee: Merck & Co., Inc., Rahway, N.J.

[21] Appl. No.: 728,019

[22] Filed: Apr. 29, 1985

[51] Int. Cl.$^4$ .......................... A61K 37/43; C07K 7/26
[52] U.S. Cl. ...................................... 514/11; 514/806; 260/112.55
[58] Field of Search ................................ 514/11, 806; 260/112.55

[56] References Cited

U.S. PATENT DOCUMENTS

| | | | |
|---|---|---|---|
| 4,235,886 | 11/1980 | Friedinger et al. | 514/11 |
| 4,310,518 | 1/1982 | Freidinger et al. | 514/11 |
| 4,505,897 | 3/1985 | Coy et al. | 514/11 |
| 4,522,813 | 6/1985 | Nutt | 514/11 |

*Primary Examiner*—Delbert R. Phillips
*Attorney, Agent, or Firm*—Salvatore C. Mitri; Michael C. Sudol

[57] ABSTRACT

Cyclic and bridged cyclic somatostatin analogs have been found to be useful as local anti-inflammatory agents in the treatment of such conditions, as, for example, psoriasis, eczema, seborrhea, and other localized inflammatory and allergic conditions.

8 Claims, No Drawings

CYCLIC AND BRIDGED CYCLIC SOMATOSTATIN ANALOGS USEFUL AS LOCAL ANTI-INFLAMMATORY AGENTS

BACKGROUND OF THE INVENTION

This invention relates to the use of cyclic and bridged cyclic somatostatin analogs as local anti-inflammatory agents for the treatment of inflammatory and allergic conditions such as, for example, psoriasis, eczema, seborrhea, and the like.

Cyclic and bridged cyclic somatostatin analogs are known compounds and are described in U.S. Pat. Nos. 4,310,518 and 4,235,886 and in European Application No. 83,111,747.8. In these U.S. Patents and the European Patent Application, these compounds are stated to be capable of inhibiting the release of glucogen, insulin, and growth hormone and reducing gastric secretions.

DESCRIPTION OF THE INVENTION

It has now been found that inflammatory and allergic conditions such as, for example, psoriasis, eczema, seborrhea, and the like, as well as atopic diseases affecting the eye such as hay fever, kerato conjunctivitis, vernal conjunctivitis, and other ocular diseases where immunological reactions to allergies are appropriate, can be treated by local; e.g., topical, application with the compounds disclosed and described in U.S. Pat. Nos. 4,310,518 and 4,235,886 and European Patent Application No. 83,111,747.8.

Therefore, this invention is directed toward the use of the cyclic and bridged cyclic somatostatin analogs disclosed and described in U.S. Pat. Nos. 4,310,518 and 4,235,886 and European Patent Application No. 83,111,747.8 for locally treating inflammatory and allergic conditions. These cyclic and bridged cyclic somatostatin analogs and the methods for their preparation disclosed and described in U.S. Pat. Nos. 4,310,518 and 4,235,886 and European Patent Application No. 83,111,747.8 are incorporated herein by reference.

Thus, the cyclic and bridged cyclic somatostatin analog compounds that can be used to locally treat inflammatory and allergic conditions according to this invention are those having the general formulae:

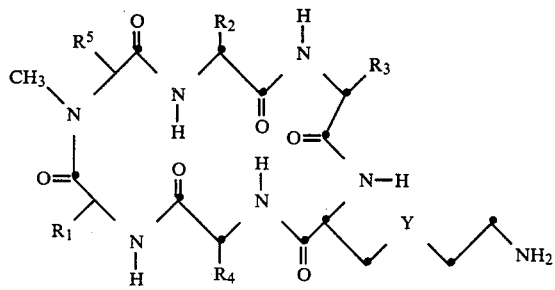

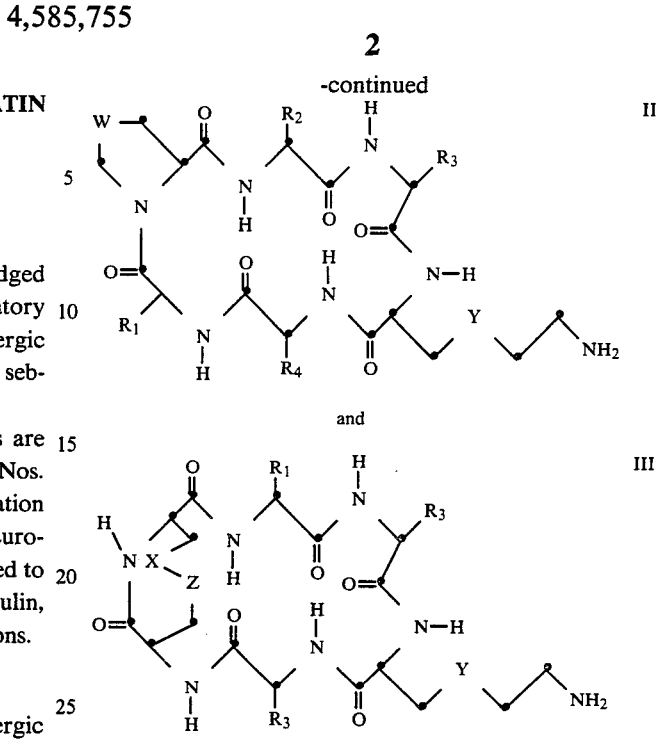

wherein in each of the compounds of Formulae I, II and III:

W is S or $(CH_2)_n$ wherein n is 0, 1, or 2;
X and Z and S or $CH_2$ provided that at least one of X or Z is S;
Y is S or $(CH_2)_m$ wherein m is 0, 1 or 2 such that the sulfur may be in any position along the chain;
$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;
$R_3$ is 3-indolylmethyl or substituted 3-indolylmethyl wherein the substituent may be loweralkyl, loweralkoxy, or halogen;
$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro; and
$R_5$ is loweralkyl, benzyl, or substituted benzyl wherein the substituent is loweralkyl, loweralkoxy, hydroxy, halogen amino or nitro.

In the Formulae I, II and III compounds, the term "loweralkyl" represents those alkyl groups either straight or branched chain, which have from 1–5 carbon atoms. Examples of such alkyl groups are methyl, ethyl, propyl, iso-propyl, butyl, sec-butyl, pentyl and the like.

The term "loweralkoxy" represents those alkoxy groups of from 1–5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" represents fluorine, chlorine, bromine and iodine.

The term "5- or 6-membered heterocyclic ring" represents those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the Formulae I, II and III compounds, there are several assymetric centers which lead to the existence of optical isomers for such compounds. For each of the assymetric centers of the various amino acids which make up these cyclic hexapeptides, both the D and L configurations are intended to be encompassed.

The following are representative cyclic hexapeptide analogs of somatostatin which can be respectively formed from the Formula I, II and III compounds above:

$$\text{N—Me—Ala—Phe—Trp} \atop \text{Phe—Thr—Lys} \qquad \text{Ia}$$

$$\text{Pro—Phe—Trp} \atop \text{Phe—Thr—Lys} \qquad \text{IIa}$$

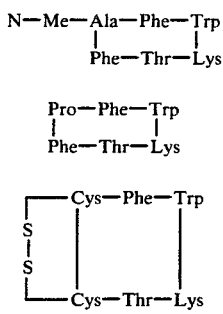   IIIa

Preferred Formula I compounds are:
(1) Cyclo-(N-Me-Ala-Tyr-D-Trp-Lys-Thr-Phe)
(2) Cyclo-(N-Me-Ala-Phe-D-Trp-Lys-Thr-Phe)
(3) Cyclo-(N-Me-Ala-Phe-L-Trp-Lys-Thr-Phe)
(4) Cyclo-(N-Me-Ala-Phe-D-Trp-Lys-Thr-p-Cl-Phe)
(5) Cyclo-(N-Me-Ala-Phe-D-5-F-Trp-Lys-Thr-Phe)
(6) Cyclo-(N-Me-Ala-Phe-L-5-F-Trp-Lys-Thr-Phe)
(7) Cyclo-(N-Me-Ala-Phe-D-Trp-Lys-Ser-Phe)
(8) Cyclo-(N-Me-Ala-Tyr-D-Trp-Lys-Val-Phe)
(9) Cyclo-(N-Me-Ala-Tyr-D-Trp-Lys-Val-Trp)
(10) Cyclo-(N-Me-Ala-Tyr-L-Trp-Lys-Val-Phe)
(11) Cyclo-(Ser-Ala-N-Me-Phe-His-D-Trp-Lys)

Preferred Formula II compounds are:
(12) Cyclo-(Pro-Tyr-D-Trp-Lys-Thr-Phe)
(13) Cyclo-(Pro-Phe-D-Trp-Lys-Thr-Phe)
(14) Cyclo-(Pro-Phe-L-Trp-Lys-Thr-Phe)
(15) Cyclo-(Pro-Phe-D-Trp-Lys-Thr-p-Cl-Phe)
(16) Cyclo-(Pro-Phe-D-5-F-Trp-Lys-Thr-Phe)
(17) Cyclo-(Pro-Phe-L-5-F-Trp-Lys-Thr-Phe)
(18) Cyclo-(Pro-Phe-D-Trp-Lys-Ser-Phe)

Preferred Formula III compounds are:

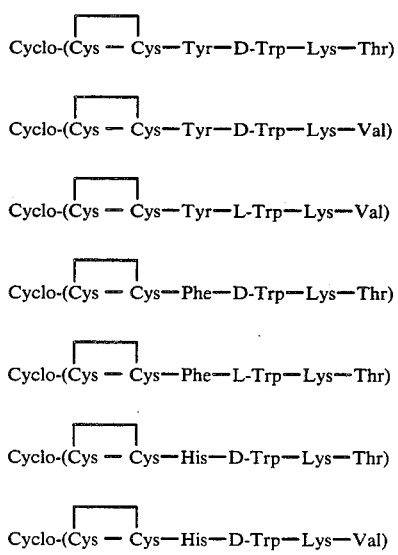

(19) Cyclo-(Cys — Cys—Tyr—D-Trp—Lys—Thr)

(20) Cyclo-(Cys — Cys—Tyr—D-Trp—Lys—Val)

(21) Cyclo-(Cys — Cys—Tyr—L-Trp—Lys—Val)

(22) Cyclo-(Cys — Cys—Phe—D-Trp—Lys—Thr)

(23) Cyclo-(Cys — Cys—Phe—L-Trp—Lys—Thr)

(24) Cyclo-(Cys — Cys—His—D-Trp—Lys—Thr)

(25) Cyclo-(Cys — Cys—His—D-Trp—Lys—Val)

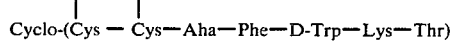

(26) Cyclo-(Cys — Cys—Aha—Phe—D-Trp—Lys—Thr)

In the instant application several abbreviated designations are used for the amino acid components and the meaning of these abbreviated designations are given below:

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tryosine |
| Val | L-valine |
| Abu | L-α-aminobutyric acid |
| Ser | L-serine |
| Asn | L-asparagine |
| Pro | L-proline |
| Asu | D- or L-aminosuberic acid |
| Cys | L-cysteine |

Local treatment of inflammatory and allergic conditions with the Formula I, II and III compounds is accomplished by providing the Formula I, II and III compounds in the form of a suitable pharmaceutical composition containing a Formula I, II or III compound or mixtures thereof as the active ingredient.

Thus, suitable pharmaceutical compositions containing the active ingredient can be in the form of creams, ointments, jellies, solutions, suspensions, sprays, eye drops, dispersible powders, and the like, and can be used to effectively treat warm blooded animals such as mice, rats, horses, dogs, cats, cattle, and the like, and humans. Such pharmaceutical compositions, in addition to an effective dosage amount of the active ingredient, typically include pharmaceutically acceptable carrier, adjuvants and vehicles.

For example, aqueous suspensions can be used containing the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension can also be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives can be employed. Suitable dispersing or wetting agents and suspending agents are exemplified by those already mentioned above. Additional excipients, for example, sweetening, flavoring and coloring agents, may also be included.

The pharmaceutical composition of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions can be in the form of an oleagenous suspension. This suspension can be formulated according to the known art using suitable dispersing or wetting agents and suspending agents which have been mentioned above.

For topical use, creams, ointments, jellies, solutions or suspensions, etc., containing the anti-inflammatory agents are employed.

The amount of active ingredient; i.e. the Formula I, II or III compound or mixtures thereof, for use in the present compositions will vary depending, for example, the condition being treated and the size and kind of mammal. Generally speaking, the active ingredient can be employed in any amount known to be an anti-inflammatory amount, as well as at doses one-fifth to one-third lower than the usual amounts for multiple daily applications.

For humans, typical effective anti-inflammatory amounts of active ingredient for use in unit dose compositions of the invention are about 0.001% to about 2.0% by weight of the composition, preferably about 0.1% to about 0.5% by weight of the composition. However, greater amounts can be employed if desired or prescribed.

DETAILED DESCRIPTION OF THE INVENTION

Protocol

The assay method employed to test the Formula I, II and III compounds as local anti-inflammatory agents is a modification of the method described by S. L. Steelman, et al. [Steroids, 1, 163 (1963)] as follows:

ASSAY 1

Assay Method

Male rats (Charles River-CD) of about 150–160 grams in weight were subcutaneously implanted in the abdominal area with two pellets each. Five animals were used per group. The pellets used were preweighed and all used in a given assay were ±1 mg from one another. The compounds were dissolved in absolute ethanol and the indicated dose applied to each pellet in 0.2 ml. The alcohol was removed in vacuo overnight. Just prior to implantation, each pellet was moistened with 0.2 ml of 0.9% saline containing 1 mg each of penicillin and streptomycin. After seven days, the pellets were dissected out together with adhering granulomatous tissue. After drying in a vacuum oven overnight at 60°–65° C., the pellets were weighed. The difference in weight between the original pellet weight and the implanted pellet weight was used as a measure of cellular proliferation (granuloma). The lower the net weight, the more anti-inflammatory activity.

The results obtained following the Assay Method described above are shown below in Table I wherein hydrocortisone was used as a positive control.

TABLE I

| Group | Dose/ Pellet | Body Wt. Change (gm) | Net weight of Pellets (mg) |
| --- | --- | --- | --- |
| Control | — | +43 | 39 ± 2.7 |
| Hydrocortisone | 200 mcg. | +44 | 34 ± 2.5 |
| Hydrocortisone | 1000 mcg. | +41 | 29 ± 2.1* |
| Compound 8 of Formula I | 10 mcg. | +43 | 39 ± 2.9 |
| Compound 8 of Formula I | 100 mcg. | +40 | 30 ± 2.4** |

± S.E. of mean
*vs Control p = <0.01
**vs Control p = <0.05

Table I above reveals that Compound 8 of Formula I exhibits significant activity at doses of 100–200 micrograms per pellet. Furthermore, no significant changes in body weights during the treatment period were noted in Assay 1.

ASSAY 2

Following the procedure described above for Assay 1, additional tests were conducted except that the compounds were administered subcutaneously as saline injections. The tests were carried out on six animals per group and the results obtained are shown below in Table II.

TABLE II

| Group | Daily Dose | Avg. body wt change (gm) | Avg. Thymus wt. (mg) | Avg. Adrenal wt. (mg) | Avg. Granuloma wt. (mg) |
| --- | --- | --- | --- | --- | --- |
| Control | — | +35 ± 2 | 552 ± 45 | 44 ± 1 | 28 ± 3 |
| Hydrocortisone | 1.0 mg | +22 ± 3** | 201 ± 20** | 36 ± 3* | 22 ± 1 |
| Hydrocortisone | 4.0 mg | −17 ± 2** | 41 ± 3** | 23 ± 1** | 19 ± 1** |
| Compound 8 of Formula I | 50 mcg | +38 ± 3 | 576 ± 14 | 43 ± 2 | 27 ± 3 |
| Compound 8 of | 200 mcg | +35 ± 2 | 571 ± 26 | 36 ±2** | 29 ± 2 |

TABLE II-continued

| Group | Daily Dose | Avg. body wt change (gm) | Avg. Thymus wt. (mg) | Avg. Adrenal wt. (mg) | Avg. Granuloma wt. (mg) |
|---|---|---|---|---|---|
| Formula I | | | | | |

± S.E. of mean
*p = <0.05
**p = <0.01

The results set forth in Table II above reveal that Compound 8 of Formula I exhibited no anti-inflammatory activity when administered subcutaneously at a total dose of 1.4 mg (0.2 mg×7). The only noticeable biological effect noted with respect to the Compound 8 of Formula I was a slight decrease in the adrenal weight of the animals tested. It will be noted that hydrocortisone exhibited its typical activity.

Comparing the results shown in Tables I and II above, it can be seen that Compound 8 of Formula I clearly exhibits anti-inflammatory activity when administered locally; i.e., topically, but no anti-inflammatory activity when administered systematically, i.e., subcutaneously.

ASSAY 3

Following the same procedure as described above for Assay 1, additional compounds were tested for local; i.e., topical, anti-inflammatory activity. The results obtained and the relative activity of these additional compounds compared to Compound 8 of Formula I are set forth in Table III below wherein the activity values of the compounds tested represent an arbitrary assignment of the order of magnitude of the compounds based upon the compound exhibiting the lowest potency. In Table III, the potency of each compound tested relative to that of somatostatin is also shown, the somatostatin (SRIF) potency being assigned a value of 1 and based upon its inhibition of growth hormone, insulin and glucogen secretion.

TABLE III

| Compound/Formula | Potency Relative to Samatostatin (SRIF) | Local Anti-inflammatory Activity |
|---|---|---|
| 8/I | 50–100 | 3+ |
| 26/III | 2–3 | 1+ |
| 13/II | 6 | 1-2+ |
| 9/I | 20–35 | 3+ |
| 10/I | 50 | 3+ |
| 11/I | 200 | 4+ |

The results shown in Table III above indicate that there appears to be a positive relationship between somatostatin (SRIF) potency and local anti-inflammatory activity.

What is claimed:

1. A method of locally treating inflammatory and allergic conditions comprising applying to the area to be treated an anti-inflammatory and anti-allergically effective amount of a compound having the Formulae:

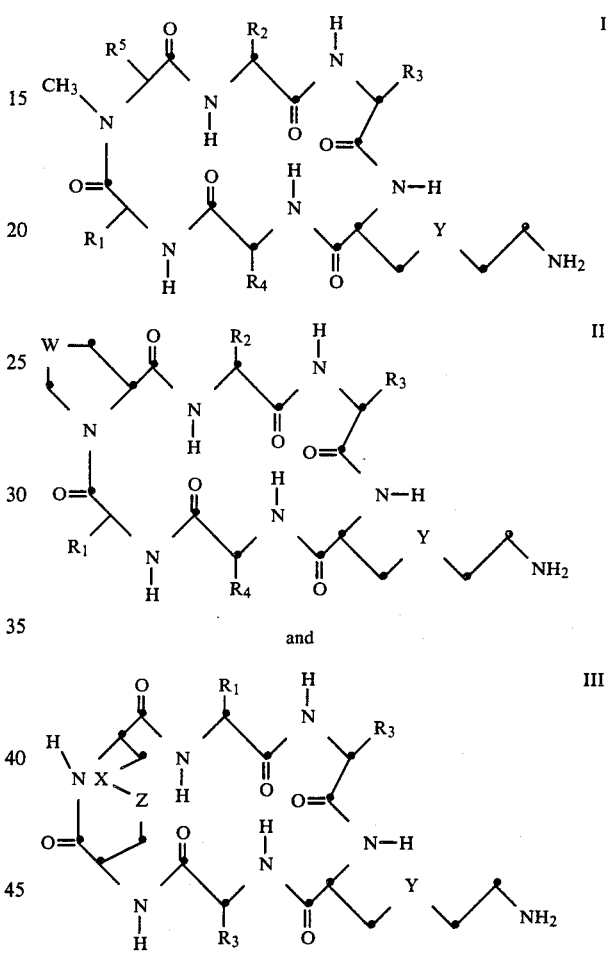

wherein in each of the compounds of Formulae I, II and III:

W is S or $(CH_2)_n$ wherein n is 0, 1, or 2;

X and Z are S or $CH_2$ provided that at least one of X or Z is S;

Y is S or $(CH_2)_m$ wherein m is 0, 1 or 2 such that the sulfur may be in any position along the chain;

$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;

$R_3$ is 3-indolylmethyl or substituted 3-indolylmethyl wherein the substituent may be loweralkyl, loweralkoxy, or halogen;

$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro; and R5 is loweralkyl, benzyl, or substituted benzyl wherein the substituent is loweralkyl, loweralkoxy, hydroxy, halogen amino or nitro.

2. The method of claim 1 wherein said Formula I compound is a member of the group:
Cyclo-(N-Me-Ala-Tyr-D-Trp-Lys-Thr-Phe);
Cyclo-(N-Me-Ala-Phe-D-Trp-Lys-Thr-Phe);
Cyclo-(N-Me-Ala-Phe-L-Trp-Lys-Thr-Phe);
Cyclo-(N-Me-Ala-Phe-D-Trp-Lys-Thr-p-Cl-Phe);
Cyclo-(N-Me-Ala-Phe-D-5-F-Trp-Lys-Thr-Phe);
Cyclo-(N-Me-Ala-Phe-L-5-F-Trp-Lys-Thr-Phe);
Cyclo-(N-Me-Ala-Phe-D-Trp-Lys-Ser-Phe);
Cyclo-(N-Me-Ala-Tyr-D-Trp-Lys-Val-Phe);
Cyclo-(N-Me-Ala-Tyr-D-Trp-Lys-Val-Trp);
Cyclo-(N-Me-Ala-Tyr-L-Trp-Lys-Val-Phe); and,
Cyclo-(Ser-Ala-N-Me-Phe-His-D-Trp-Lys).

3. The method of claim 1 wherein said Formula II compound is a member of the group:
Cyclo-(Pro-Tyr-D-Trp-Lys-Thr-Phe);
Cyclo-(Pro-Phe-D-Trp-Lys-Thr-Phe);
Cyclo-(Pro-Phe-L-Trp-Lys-Thr-Phe);
Cyclo-(Pro-Phe-D-Trp-Lys-Thr-p-Cl-Phe);
Cyclo-(Pro-Phe-D-5-F-Trp-Lys-Thr-Phe);
Cyclo-(Pro-Phe-L-5-F-Trp-Lys-Thr-Phe); and,
Cyclo-(Pro-Phe-D-Trp-Lys-Ser-Phe).

4. The method of claim 1 wherein said Formula III compound is a member of the group:

Cyclo-(Cys — Cys—Tyr—D-Trp—Lys—Thr);

Cyclo-(Cys — Cys—Tyr—D-Trp—Lys—Val);

Cyclo-(Cys — Cys—Tyr—L-Trp—Lys—Val);

Cyclo-(Cys — Cys—Phe—D-Trp—Lys—Thr);

Cyclo-(Cys — Cys—Phe—L-Trp—Lys—Thr);

Cyclo-(Cys — Cys—His—D-Trp—Lys—Thr);

Cyclo-(Cys — Cys—His—D-Trp—Lys—Val); and,

Cyclo-(Cys — Cys—Aha—Phe—D-Trp—Lys—Thr).

5. A method of locally treating atopic eye diseases comprising applying to the area to be treated an anti-atopically effective amount of a compound having the Formulae:

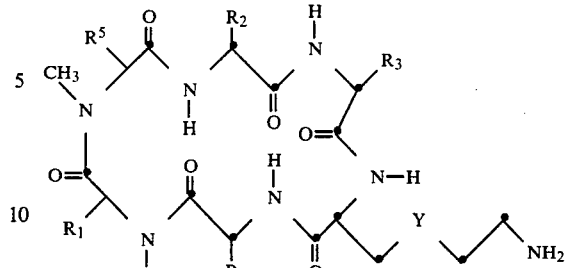
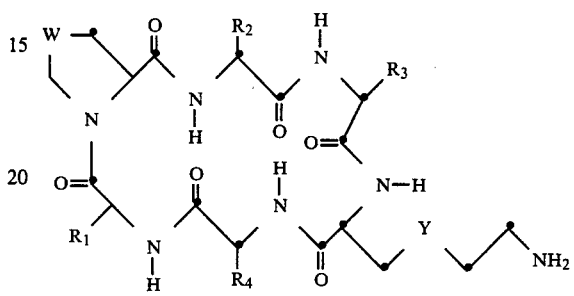
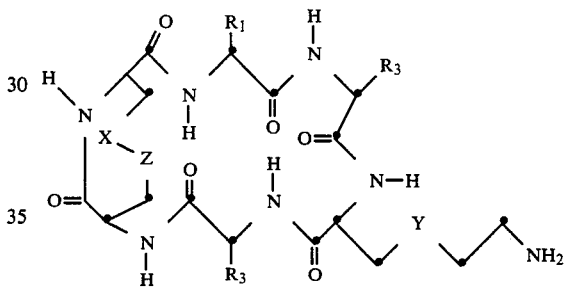

wherein in each of the compounds of Formulae I, II and III:
W is S or $(CH_2)_n$ wherein n is 0, 1, or 2;
X and Z are S or $CH_2$ provided that at least one of X or Z is S;
Y is S or $(CH_2)_m$ wherein m is 0, 1 or 2 such that the sulfur may be in any position along the chain;
$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;
$R_3$ is 3-indolylmethyl or substituted 3-indolylmethyl wherein the substituent may be loweralkyl, loweralkoxy, or halogen;
$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro; and
$R_5$ is loweralkyl, benzyl, or substituted benzyl wherein the substituent is loweralkyl, loweralkoxy, hydroxy, halogen amino or nitro.

6. The method of claim 5 wherein said Formula I compound is a member of the group:
Cyclo-(N-Me-Ala-Tyr-D-Trp-Lys-Thr-Phe);
Cyclo-(N-Me-Ala-Phe-D-Trp-Lys-Thr-Phe);
Cyclo-(N-Me-Ala-Phe-L-Trp-Lys-Thr-Phe);
Cyclo-(N-Me-Ala-Phe-D-Trp-Lys-Thr-p-Cl-Phe);

Cyclo-(N-Me-Ala-Phe-D-5-F-Trp-Lys-Thr-Phe);
Cyclo-(N-Me-Ala-Phe-L-5-F-Trp-Lys-Thr-Phe);
Cyclo-(N-Me-Ala-Phe-D-Trp-Lys-Ser-Phe);
Cyclo-(N-Me-Ala-Tyr-D-Trp-Lys-Val-Phe);
Cyclo-(N-Me-Ala-Tyr-D-Trp-Lys-Val-Trp);
Cyclo-(N-Me-Ala-Tyr-L-Trp-Lys-Val-Phe); and,
Cyclo-(Ser-Ala-N-Me-Phe-His-D-Trp-Lys).

7. The method of claim 5 wherein said Formula II compound is a member of the group:
Cyclo-(Pro-Tyr-D-Trp-Lys-Thr-Phe);
Cyclo-(Pro-Phe-D-Trp-Lys-Thr-Phe);
Cyclo-(Pro-Phe-L-Trp-Lys-Thr-Phe);
Cyclo-(Pro-Phe-D-Trp-Lys-Thr-p-Cl-Phe);
Cyclo-(Pro-Phe-D-5-F-Trp-Lys-Thr-Phe);
Cyclo-(Pro-Phe-L-5-F-Trp-Lys-Thr-Phe); and,
Cyclo-(Pro-Phe-D-Trp-Lys-Ser-Phe).

8. The method of claim 5 wherein said Formula III compound is a member of the group:

Cyclo-(Cys—Cys—Tyr—D-Trp—Lys—Thr);

Cyclo-(Cys—Cys—Tyr—D-Trp—Lys—Val);

Cyclo-(Cys—Cys—Tyr—L-Trp—Lys—Val);

Cyclo-(Cys—Cys—Phe—D-Trp—Lys—Thr);

Cyclo-(Cys—Cys—Phe—L-Trp—Lys—Thr);

Cyclo-(Cys—Cys—His—D-Trp—Lys—Thr);

Cyclo-(Cys—Cys—His—D-Trp—Lys—Val); and,

Cyclo-(Cys—Cys—Aha—Phe—D-Trp—Lys—Thr).

* * * * *